United States Patent
Zhang et al.

(10) Patent No.: US 9,513,266 B2
(45) Date of Patent: Dec. 6, 2016

(54) GAS CHROMATOGRAPH-ION MOBILITY SPECTROMETER SYSTEM

(71) Applicant: Nuctech Company Limited, Beijing (CN)

(72) Inventors: Qingjun Zhang, Beijing (CN); Yuanjing Li, Beijing (CN); Zhiqiang Chen, Beijing (CN); Qiufeng Ma, Beijing (CN); Ziran Zhao, Beijing (CN); Yinong Liu, Beijing (CN); Yaohong Liu, Beijing (CN); Xiang Zou, Beijing (CN); Yanchun Wang, Beijing (CN); Junxiao Wang, Beijing (CN); Jianping Chang, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 14/577,653

(22) Filed: Dec. 19, 2014

(65) Prior Publication Data

US 2015/0185190 A1 Jul. 2, 2015

(30) Foreign Application Priority Data

Dec. 27, 2013 (CN) .......................... 2013 1 0741366

(51) Int. Cl.
*H01J 49/00* (2006.01)
*G01N 30/72* (2006.01)
(Continued)

(52) U.S. Cl.
CPC ........ *G01N 30/7206* (2013.01); *G01N 27/622* (2013.01); *G01N 27/64* (2013.01); *H01J 49/0422* (2013.01)

(58) Field of Classification Search
None
See application file for complete search history.

(56) References Cited

U.S. PATENT DOCUMENTS 3,372,298 A * 3/1968 Merryman ............... H04N 9/27 313/450
5,083,019 A * 1/1992 Spangler .............. G01N 1/2247 250/282

(Continued)

FOREIGN PATENT DOCUMENTS

CN 101728208 A 6/2010
CN 201917559 U * 8/2011

(Continued)

OTHER PUBLICATIONS

Siegel, "Atmospheric Pressure Ionization," Plasma Chromatography, Plenum Press, NY, 1984, Chapter 3, pp. 95-113.

(Continued)

*Primary Examiner* — Andrew Smyth
(74) *Attorney, Agent, or Firm* — Oliff PLC

(57) ABSTRACT

A GC-IMS system is disclosed. The system includes a sample transfer device. The sample transfer device connects the gas chromatograph to the reaction region and, the sample from the gas chromatograph is transferred to the reaction region by the sample transfer device. With the GC-IMS system, generation of sample molecular ion fragments can be avoided so that the spectrum is easily identified; moreover, the application field of the GC-IMS system is extended to a range of analysis of organic macromolecule samples which have a high polarity, are difficult to volatilize, and are thermally instable. On the other hand, the GC-IMS system overcomes the defect of ion destruction due to neutralization reaction among positive and negative ions so as to evade the detection.

16 Claims, 1 Drawing Sheet

(51) Int. Cl.
*G01N 27/62* (2006.01)
*G01N 27/64* (2006.01)
*H01J 49/04* (2006.01)

(56) References Cited

U.S. PATENT DOCUMENTS

| | | | | |
|---|---|---|---|---|
| 5,811,059 | A * | 9/1998 | Genovese | G01N 30/10 250/287 |
| 6,479,652 | B1 * | 11/2002 | Crameri | C07K 14/005 435/440 |
| 6,481,263 | B1 * | 11/2002 | Haley | G01N 27/622 250/287 |
| 6,627,878 | B1 * | 9/2003 | Machlinski | G01N 1/2202 250/286 |
| 2004/0079879 | A1 * | 4/2004 | Ross | H01J 49/168 250/287 |
| 2005/0051719 | A1 * | 3/2005 | Miller | G01N 27/622 250/287 |
| 2005/0211894 | A1 * | 9/2005 | Laprade | G01N 27/622 250/287 |
| 2011/0272574 | A1 * | 11/2011 | Mitko | G01N 27/622 250/287 |
| 2012/0138783 | A1 * | 6/2012 | Peng | G01N 27/622 250/282 |
| 2013/0009053 | A1 * | 1/2013 | Wu | G01N 27/622 250/282 |
| 2015/0185190 | A1 * | 7/2015 | Zhang | G01N 27/64 250/288 |

FOREIGN PATENT DOCUMENTS

| | | | |
|---|---|---|---|
| DE | 195 02 674 C1 | 9/1996 | |
| JP | S64-79652 A | 3/1989 | |
| WO | 2009/094059 A2 | 7/2009 | |
| WO | WO 2009094059 A2 * | 7/2009 | G01N 27/622 |
| WO | WO 2009094059 A3 * | 12/2009 | G01N 27/622 |
| WO | 2012/056709 A1 | 5/2012 | |

OTHER PUBLICATIONS

Baumbach et al., "Exploration of a Multicapillary Column for Use in Elevated Speed Gas Chromatography," International Journal of Environmental Analytical Chemistry, 1997, vol. 66, pp. 225-239.
Cook et al., "Using Gas Chromatography with Ion Mobility Spectrometry to Resolve Explosive Compounds in the Presence of Interferents," Journal of Forensic Sciences, Nov. 2010, vol. 55, No. 6, pp. 1582-1591.
May 18, 2015 Office Action received in European Application No. 14199286.7.

* cited by examiner

GAS CHROMATOGRAPH-ION MOBILITY SPECTROMETER SYSTEM

CROSS-REFERENCE TO RELATED APPLICATION

This application claims the benefit of Chinese Patent Application No. 201310741366.X filed on Dec. 27, 2013 in the State Intellectual Property Office of China, the whole disclosure of which is incorporated herein by reference.

BACKGROUND OF THE INVENTION

1. Field of the Invention

Embodiments of the present invention relate to a gaschromatograph-ion mobility spectrometer (GC-IMS) system.

2. Description of the Related Art

U.S. Pat. No. 5,811,059A and U.S. Pat. No. 6,481,263B1 each disclose a gas analyzing apparatus which comprises a gas chromatograph (GC) and a single-mode ion mobility spectrometer (IMS). The apparatus has a better separation capacity than a simple IMS.However, it is only used To detect charged particles of a single polarity, but neither be used to detect both positive and negative ions simultaneously, nor be used to detect those substances having opposite electroaffinities. DE19502674C1 discloses a method for measuring both positive and negative ions by switching of an electric field. Although both the positive and negative ions are measured, they are not simultaneously measured due to a switching time interval, so that correlative information of the positive and negative ions will be lost during the measurement. CN201917559U discloses a gas analyzing apparatus which comprises a gas chromatograph (GC) and a dual-mode ion mobility spectrometer (IMS), wherein both positive and negative ions of a mixture are detected simultaneously. However, in the gas analyzing apparatus comprising the gas chromatograph and the IMS, as those disclosed in patent documents including CN201917559U and U.S. Pat. No. 5,811,059A, a sample separated by the GC is introduced directly into an ionization region. An ionization source is a main functional component of the IMS. Ionization effects generated by different ionization sources have a very direct influence on performance of the IMS. For example, all of the most widely used 13-sources will emit high-energy primary electrons (of 67 keV for $^{63}$Ni and of 18 keV for $^{3}$H). If the structural design in which a sample is introduced directly into the ionization region is used, when the sample passes through in the vicinity of the β-source, it will be hit by high-energy β-particles directly into molecular ion fragments, or will be ionized into positively charged sample molecular ions. On one hand, the sample molecular ion fragments will cause a rise in Reaction Ion Peak (RIP), disturb a baseline or generate interference peaks, and reduce IMS resolution. A hard ionization source will generate complicated fragments and generate a spectrum which is difficult to discriminate, especially for biological macromolecules such as proteins and nucleic acids. As a result, it is difficult to extend the application field of the GC-IMS system to the detection field of organic macromolecules. On the other hand, the sample molecular ion fragments or the positively charged sample molecular ions will further react with reactive ions to generate unidentifiable ion mobility spectrum, which disorders spectral lines and seriously affects analysis of the spectral lines. If a pulsed corona discharge ionization source, as another most widely used ionization source, is used, the corona discharge belongs to soft ionization (primary electrons of 5 eV-10 eV), and thus it will not hit sample molecules into fragments. However, the sample molecules passing through in the vicinity of a corona needle will be ionized into positively charged sample molecular ions, and the positively charged sample molecular ions may react with unionized carrier gas molecules, which increases complexity of sample analysis and even disturbs peak analysis. Furthermore, the positively charged sample molecular ions maybe destroyed due to the neutralization reaction with negative reactive ions, so that the detection is evaded. In addition to the problems caused by the above design defects, conventional dual-mode IMS (CN201917559U) and single-mode IMS (U.S. Pat. No. 5,811,059A) have another design defect, that is, positive and negative ions generated in the ionization region are not separated from each other when entering a reaction region. When carrier gas is ionized by the ionization source, both positive ions (mainly, $(H_2O)_nH^+$) and negative ions (mainly, $O_2^-(H_2O)_2$) will be simultaneously generated. Coulomb attraction forces will be generated among the positive ions and the negative ions generated in a same space of the ionization region. If no repulsion voltage is applied to the ionization region, the positive ions and the negative ions (or electrons) driven to enter the reaction region by a carrier gas flow will be neutralized due to their collision and recombination. This reaction region will become a trap where the positive ions and the negative ions are destroyed. Even if a repulsion voltage is applied to the ionization region in order to separate the ions having different charges, there is a loss caused by neutralization due to recombination of the ions [Siegel, M W, *Atmospheric pressure ionization, in Plasma Chromatography*, Carr, T W, Ed., Plenum Press, New York, 1984, chap. 3, pp. 95-113.]. Therefore, such structural design will result in a reaction ion loss, thereby resulting in a low baseline signal, and a decreased detection sensitivity of the IMS.

SUMMARY OF THE INVENTION

In an embodiment of the present invention, there is provided a GC-IMS system, comprising: a gas chromatograph, an IMS comprising: an ionization region for ionizing a gas such as carrier gas to generate ions, and a reaction region which is adjacent to and different from the ionization region and is configured for combining the ions with a sample, and a sample transfer device which connects the gas chromatograph to the reaction region and by which the sample from the gas chromatograph is transferred to the reaction region directly, instead of through the ionization region or by which the sample from the gas chromatograph is transferred to the reaction region directly by bypassing the ionization region.

In an embodiment of the present invention, there is provided an IMS comprising: a ionization region for ionizing a gas to generate ions, a reaction region which is adjacent to and different from the ionization region and is configured for combining the ions with a sample, and a sample transfer device by which the sample is transferred to the reaction region directly, instead of through the ionization region or by which the sample from the gas chromatograph is transferred to the reaction region directly by bypassing the ionization region.

DETAILED DESCRIPTION OF THE EMBODIMENTS

A further description of the invention will be made as below with reference to embodiments of the present invention taken in conjunction with the accompanying drawings.

Figure 1:
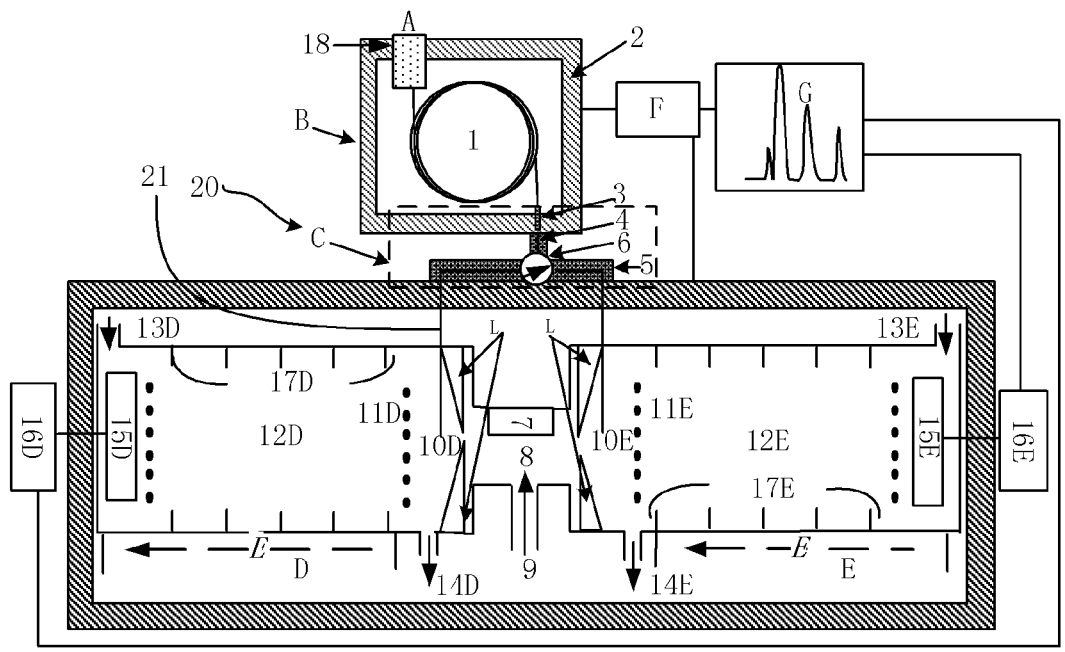
FIG. 1 is a schematic diagram of a GC-IMS system according to an embodiment of the present invention.

As shown in FIG. 1, a GC-IMS system according to an embodiment of the present invention comprises a GC, an IMS, and an interface C between the GC and the IMS.

As shown in FIG. 1, the gas chromatograph comprises: a sample injector A, a GC separation column system B, and a transfer unit 3.

As shown in FIG. 1, the IMS comprises: a ionization region 8 for ionizing a gas such as carrier gas (for example, air or nitrogen gas) to generate ions, and reaction regions 10D and 10E which are adjacent to and different from the ionization region 8 and are configured for combining the ions with a sample (such as sample molecules), and a sample transfer device 20 which connects the gas chromatograph to the reaction regions 10D and 10E and by which the sample from the gas chromatograph is transferred to the reaction regions 10D and 10E directly, instead of through the ionization region 8 or by which the sample from the gas chromatograph is transferred to the reaction region 10D and 10E directly by bypassing the ionization region 8. The sample transfer device 20 comprises the interface C between the GC and the IMS, a conduit 21 for transferring a sample; and a flow divider valve 6 disposed on the conduit 21 and configured to adjust amounts of the sample to be respectively transferred to the two reaction regions 10D and 10E.

The sample transfer device 20 may be any appropriate sample transfer device so long as a sample from the gas chromatograph can be transferred to the reaction regions 10D and 10E directly, instead of through the ionization region 8 or a sample from the gas chromatograph can be transferred to the reaction regions 10D and 10E directly by bypassing the ionization region 8.

The IMS further comprises electrodes L. The electrodes L are disposed substantially between the ionization region 8 and the reaction regions 10D and 10E and are configured to generate an electric field for moving positive ions and negative ions of the ions generated in the ionization region 8 into the reaction regions 10D and 10E.

As shown in FIG. 1, the IMS is a dual-mode IMS which comprises a positive-mode drift tube 12D and a negative-mode drift tube 12E, and which comprises the two reaction regions 10D and 10E adjacent to the ionization region 8, and the two electrodes L are respectively disposed substantially between the ionization region 8 and one 10D of the two reaction regions and between the ionization region 8 and the other 10E of the two reaction regions and are configured to generate electric fields for respectively moving positive ions and negative ions of the ions generated in the ionization region 8 into the two reaction regions 10D and 10E. The electrodes L may have a horn shape.

Assumption that the IMS is a single-mode IMS, the sample transfer device 20 connects the gas chromatograph to the reaction region (single reaction region) such that a sample from the gas chromatograph is transferred to the reaction region directly, instead of through the ionization region 8 or a sample from the gas chromatograph is transferred to the reaction region directly by bypassing the ionization region 8. The sample transfer device 20 comprises the interface C between the GC and the IMS, a conduit 21 for transferring the sample; and a valve 6 disposed on the conduit 21 and configured to adjust an amount of the sample to be transferred to the reaction region.

In the embodiment of the present invention, as shown in FIG. 1, the GC is used as a front-end primary separator of the IMS. The sample separated by the GC is divided into two streams of sample, under the control of the flow divider valve 6 such as a proportional flow divider valve. The two steams of sample pass through the two positive-mode and negative-mode drift tubes of the TMS at any angles and enter the two reaction regions 10D and 10E of the IMS, respectively. In this way, the sample separated by the GC can bypass the ionization region 8 of the IMS. Therefore, not only sample molecules are prevented from being hit into ion fragments to interfere with the spectrum, but the defects of ion destruction due to neutralization reaction among positive and negative ions and the sensitivity reduction are also prevented. The IMS is used as a detector of the GC and comprises the positive-mode drift tube and the negative-mode drift tube, and thus can detect positive and negative ions simultaneously.

As shown in FIG. 1, the GC-IMS system further comprises an electric control system F, a GC-IMS signal acquisition and analysis system G, and a carrier gas system (a GC carrier gas 18, a sweeping gas 9 of IMS, the drift gases 13D and 13E of IMS, and the drift outflow gases 14D and 14E of IMS).

As shown in FIG. 1, the sample injector A is an input device of the GC-IMS system. Various sample injectors which are suitable for feeding a sample into the GC may be selected as the sample injector A, according to the requirements of properties of a substance to be analyzed and the sample injector A is convenient in joint and replacement. The GC separation column system B comprises a separation column 1 and a temperature control case 2. The separation column 1 may be a packed column, a capillary column, a multi-capillary column (MCC), and the like. The RT of the GC separation column depends upon the type of the separation column. The RT of the most widely used capillary column is of the order of magnitude of hours, can provide wider separation capacity, and can be used in legal inspection. The multi-capillary column [J. I. Baumbach, G. A. Eiceman, D. Klockow, S. Sielemann, A. vIrmer: *Exploration of a multicapillary column for use in elevated speed chromatography. Int. J Env. Anal. Chem.* 66, 225-240, (1997)] shortens the RT (RT of the multi-capillary column is of the order of magnitude of seconds to minutes) while ensuring a big amount of a sample injection, and can be used in quick inspection. The temperature control case functions to control an operating temperature of the separation column I accurately, thereby ensuring that a sample is accurately analyzed and can be repeatedly separated.

A conventional radioactive source may be adopted as the ionization source of the IMS. The ionization source such as a corona discharge device, a glow discharge device, a laser ionization device, and a surface ionization device may also be adopted. For convenience the ionization source 7 is shown in FIG. 1 in the form of a radioactive source. The two horn shaped electrodes L are disposed in the two drift tubes. The IMS may be the dual-mode IMS disclosed in CN101728208A, or any other conventional dual-mode IMS.

As shown in FIG. 1, at the interface C between the GC and the IMS,a transfer standard part for the GC separation column may be used as the transfer unit 3 at an end of the GC separation column 1. The transfer unit 3 may also be a self-designed part which is convenient to assemble and disassemble. A metal transfer column 4 may be any metal columns of which an inner wall is smooth and is subjected to a deactivation process, such as an aluminum alloy column, and an MXT column [Cook G W, LaPuma P T, Hook G L, et al. *Using gas chromatography with ion mobility spectrometry to resolve explosive compounds in the presence of interferents[J]. Journal of forensic sciences*, 2010, 55(6): 1582.]. The transfer column 4 needs to be heated by an additional heating transfer pipe 5, thereby ensuring an internal temperature of the transfer column 4 is higher than that of the separation column and thus preventing the sample flowing from the GC separation column from condensing in the transfer column and ensuring that the sample molecules enter the IMS without any loss. The proportional flow divider valve 6 is a commonly used flow divider valve, and also enables the flow rate to be proportionally adjustable.

The carrier gas system of the IMS-GC system comprises two parts. One part is used for allowing high-purity carrier gas 18 to enter the GC separation column and may include a pipe and a valve for GC which are currently commonly used. The other part is used for the carrier gas of the IMS, and generally, a normal-pressure pure air is selected as the carrier gas. The carrier gas of the IMS comprises a stream of sweeping gas 9, two streams of drift carrier gases 13D and 13E, and two steams of outflowing gases 14D and 14E.

The electric control system F is in charge of controlling the heating of the GC and the temperature of the GC, the heating, a high-voltage power supply, and a power supply of a preamplifier of the IMS, valves and pumps; and is also in charge of transmitting signals measured by the IMS to a peripheral device.

A measurement process of the GC-IMS system will be described as below with reference to FIG. 1. A sample is introduced by the sample injector A, and the sample, together with its GC carrier gas 18, enters the separation column 1. The mixed sample is separated into individual components under the action of the separation column and flows out from the end of the GC separation column. The sample then enters the transfer column 4 through the transfer unit 3. An outer surface of the transfer column 4 is armored by the heating transfer pipe 5. The proportional flow divider valve 6 is disposed at a middle of the transfer column 4, and is in charge of dividing the sample into two steams of sample. The two steams of sample enter the two reaction regions 10D and 10E of the IMS, respectively. At the same time, mixed positive and negative reactive ions generated in the ionization region 8 are respectively pulled to the two reaction regions 10D and 10E under the sweeping action of the sweeping gas 9 in cooperation with the action of the two horn shaped electrodes L. As a result, the positive and negative ions are separated. In the two reaction regions 10D and 10E, the reactive ions carried by the sweeping gas 9 (flowing at a flow rate of 0-0.5 L/min) meet and are sufficiently mixed with the high-speed positive-pressure gas stream flowing out from the GC under the action of the upstream flows of drift gases 13D and 13E. Sample molecules have different electroaffmities. Therefore, sample molecules having stronger electro negativity are positively charged by means of prototropy in the reaction region 10D and are stored in a storage region formed in the horn shaped electrode L. Likewise, sample molecules having stronger electropositivity are combined with the negative reactive ions to be negatively charged in the reaction region 10E and are stored in a storage region formed in the horn shaped electrode L. By opening the ion gates 11D and 11E, the stored ions are pulled into drift regions 12D and 12E, respectively. The charged ions distance one another and reach Faraday plates 15D and 15E in succession, depending on their drift speeds under the action of electric fields of the drift regions. Current signals acquired by the Faraday plates 15D and 15E are transmitted through the amplifier circuits and analog-digital converters 16D and 16E to the signal acquisition and analysis system G for data processing. The signal acquisition and analysis system G acquires and stores all of ion spectral data during the entire separation performed by the GC-IMS. In one complete measurement, the signal acquisition and analysis system simultaneously records an IMS drift amplitude versus time (of which the unit is millisecond) spectrum, a GC RT (of which the unit is second) spectrum, and a three-dimensional GC-IMS drift time versus RT versus amplitude spectrum. The three spectrums are simultaneously monitored so that more information can be provided and the analysis capability of the system can be improved. In other words, some substance that cannot be separated by the GC can be separated by the IMS, and vice versa. Therefore, the GC-IMS system is comparable in function to a combination of a GC and a mass spectrometer (MS) in series. In the conventional GC-MS, in order to prevent sample molecules from being hit into fragments, a soft ionization technique (matrix-assisted laser desorption or electrospray ionization (ESI) technique) which is high in technical difficulty and expensive in cost is generally adopted. However, with the GC coupled to dual-mode IMS system according to the embodiment of the present invention, generation of the molecular ion fragments is avoided without any particular design requirement of the ionization technique, and the application field of the GC-IMS system is extended to the field of detection of organic macromolecules. Furthermore, the GC coupled to dual-mode IMS system can simultaneously measure positive and negative ions, while the conventional GC-MS can detect only positive ions. For those substances that simultaneously generate positive and negative ions, the GC coupled to dual-mode IMS system will greatly increase an ability of identification of the substances and enhance IMS resolution.

Figure 2:
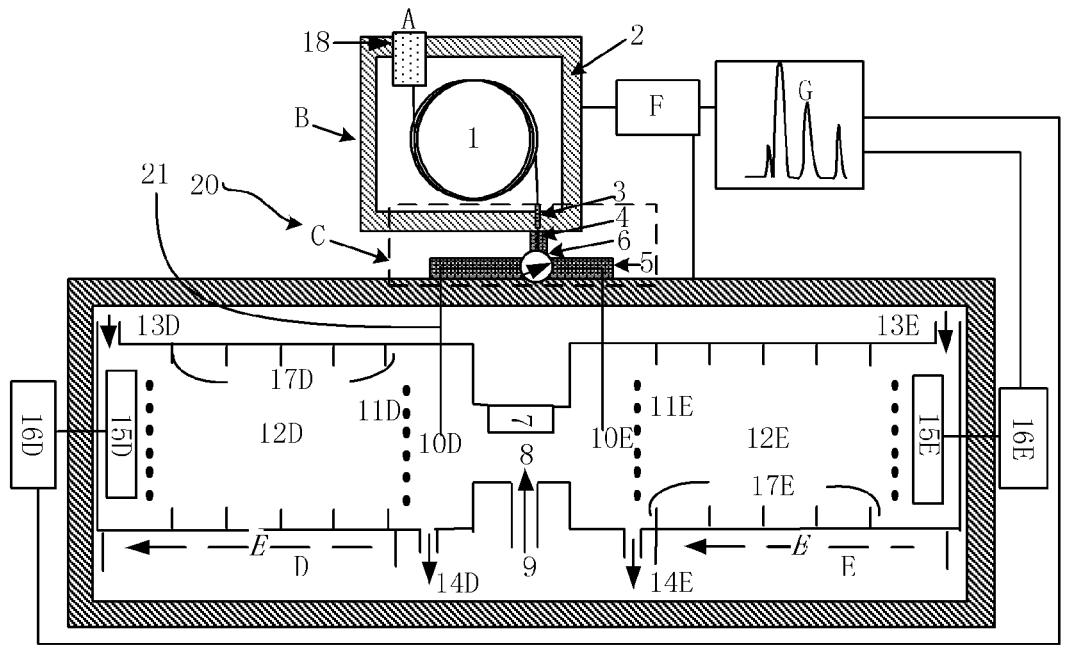
FIG. 2 is a schematic diagram of a GC-IMS system according to another embodiment of the present invention.

FIG. 2 shows a GC-IMS system according to another embodiment of the present invention. The GC-IMS system shown in FIG. 2 is the same as that shown in FIG. 1, except that the GC-IMS system shown in FIG. 2 does not include the two horn shaped electrodes L. In the embodiment shown in FIG. 2, the sample separated by the GC are also introduced directly into the reaction regions 10D and 10E of the IMS, respectively, thereby avoiding generation of ion fragments. The embodiment shown in FIG. 2 is slightly different from that shown in FIG. 1 in that, in the embodiment shown in FIG. 2, when the ion gates 11D and 11D are opened, the ions in the reaction regions are detected; while when the ion gates are closed, the reactive ions are not stored, but are lost on walls of the drift tubes. The other detection processes of the system shown in FIG. 2 are the same as those of the system shown in FIG. 1.

Furthermore, the inventive concept according to the embodiments of the present invention is also applicable to an IMS. Therefore, the IMS according to an embodiment of the present invention comprises: an ionization region 8 for ionizing IMS carrier gas to generate ions, a reaction region 10D, 10E which is adjacent to and different from the ionization region 8 and is configured for combining the ions with a sample, and a sample transfer device 20 by which the sample is transferred to the reaction region 10D, 10E directly, instead of through the ionization region 8 or by which the sample is transferred to the reaction region 10D, 10E directly by bypassing the ionization region 8. The sample transfer device 20 may be a conduit which is additionally disposed to a convention sample feed device and by which a sample is transferred directly to the reaction region 10D, 10E. The IMS further comprises: an electrode L disposed substantially between the ionization region 8 and the reaction region 10D, 10E and configured to generate an electric field for moving positive ions or negative ions of the ions generated in the ionization region 8 into the reaction region 10D, 10E. The IMS may be either a single-mode IMS, or a dual-mode IMS. If the IMS is a dual-mode IMS, the IMS comprises two reaction regions adjacent to the ionization region, and two electrodes L respectively disposed substantially between the ionization region and one of the two reaction regions and between the ionization region and the other of the two reaction regions and configured to generate electric fields for respectively moving positive ions and negative ions of the ions generated in the ionization region into the two reaction regions. The electrodes L may have a horn shape.

As described above, if the IMS is a single-mode IMS, the IMS comprises one reaction region and may further comprise one electrode L.

These embodiments of the present invention provides aGC-IMS system, by which generation of sample molecular ion fragments or ionization of sample molecules into positively charged molecular ions are avoid and thus detection sensitivity is effectively increased.

In an embodiment of the present invention, there is provided a GC-IMS system, comprising: a gas chromatograph, an IMS comprising: an ionization region for ionizing a gas such as carrier gas to generate ions, and a reaction region which is adjacent to and different from the ionization region and is configured for combining the ions with a sample, and a sample transfer device which connects the gas chromatograph to the reaction region and by which the sample from the gas chromatograph is transferred to the reaction region directly, instead of through the ionization region or by which the sample from the gas chromatograph is transferred to the reaction region directly by bypassing the ionization region.

In an embodiment of the present invention, the IMS further comprises: an electrode disposed substantially between the ionization region and the reaction region and configured to generate an electric field for moving positive ions or negative ions of the ions generated in the ionization region into the reaction region.

In an embodiment of the present invention, the IMS comprises a dual-mode IMS comprising two reaction regions adjacent to the ionization region, and the IMS further comprises: two electrodes respectively disposed substantially between the ionization region and one of the two reaction regions and between the ionization region and the other of the two reaction regions and configured to generate electric fields for respectively moving positive ions and negative ions of the ions generated in the ionization region into the two reaction regions.

In an embodiment of the present invention, the electrode has a horn shape.

In an embodiment of the present invention, the sample transfer device further comprises a conduit for transferring the sample; and a flow divider valve disposed on the conduit and configured to adjust amounts of the sample to be respectively transferred to the two reaction regions.

In an embodiment of the present invention, the carrier gas may be air or nitrogen gas.

In an embodiment of the present invention, there is provided an IMS comprising: a ionization region for ionizing a gas to generate ions, a reaction region which is adjacent to and different from the ionization region and is configured for combining the ions with a sample, and a sample transfer device by which the sample is transferred to the reaction region directly, instead of through the ionization region or by which the sample from the gas chromatograph is transferred to the reaction region directly by bypassing the ionization region.

In an embodiment of the present invention, the IMS further comprises: an electrode disposed substantially between the ionization region and the reaction region and configured to generate an electric field for moving positive ions or negative ions of the ions generated in the ionization region into the reaction region.

In an embodiment of the present invention, the IMS is a dual-mode IMS, and the reaction region comprises two reaction regions adjacent to the ionization region, and the IMS further comprises: two electrodes respectively disposed substantially between the ionization region and one of the two reaction regions and between the ionization region and the other of the two reaction regions and configured to generate electric fields for respectively moving positive ions and negative ions of the ions generated in the ionization region into the two reaction regions.

In an embodiment of the present invention, the electrode has a horn shape.

In some embodiments of the present invention, on one band, the GC-IMS system achieves simultaneous detection of positive and negative ions, interrelates these positive-mode and negative-mode spectrums, and has a higher ability to separate some substances than a single-tube IMS which achieves positive and negative modes by switching a voltage. Furthermore, with the GC-IMS system, generation of sample molecular ion fragments can be avoided so that the spectrum is simple and can be easily identified thereby, object molecules can be more accurately detected and thus its identifying capability can be effectively improved. As a result, the application field of this GC-IMS system is extended to a range of analysis of organic macromolecule samples which have a high polarity, are difficult to volatilize, and are thermally instable. On the other hand, with the GC-IMS system, the defect of ion destruction due to neutralization reaction among positive and negative ions so as to evade the detection is overcome, and thus detection sensitivity is effectively increased.

In some embodiments of the present invention, the GC-IMS system has the advantages of both the GC and the dual-mode IMS. The GC may be conventional separation instrument. In the GC, a gaseous sample together with carrier gas passes through a separation column where a stationary phase is disposed. Residence time (RT), during which compositions of the sample respectively pass through the separation column, of these compositions of the sample are different from one another because interactions between different compositions of the sample and molecules of the stationary phase are different from one another. In the GC, substance is discriminated based on its RT characteristic. The RT of the GC is of the order of magnitude of minutes (several minutes to tens of minutes), and a minimum peak width is less than twenty seconds. Because ion mobility spectra are obtained at a frequency of 20 to 50 Hz, many IMS spectra can be obtained for each chromatographic peak. Therefore, the GC and the IMS can be combined together such that the GC is used as a primary separator of the IMS while the IMS is used as a detector of the GC.

In some embodiments of the present invention, the IMS comprises a positive-mode drift tube and a negative-mode drift tube, and an ionization region is disposed between two reaction regions of the two drift tubes. The two drift tubes share the single ionization region. In this way, not only one ionization source is saved, but calibration between two ionization sources and accurate proportioning between amounts of a sample entering two ionization regions are also omitted. Two horn shaped electrodes may be disposed on both sides of the ionization region, respectively. The electrodes generate electric fields. Alternatively, the two electrodes may not be disposed. When there are the two horn shaped electrodes, the two electric fields can separate positive ions from the negative ions, so that the problem of ion destruction due to neutralization reaction among positive and negative ions can be effectively alleviated. Other designs of the IMS may be based on CN101728208A, or other conventional dual-mode IMS.

An interface between the GC and the IMS serves as a transfer passage for introducing a sample separated by the separation column of the GC into the reaction regions of the IMS, without any loss. The sample separated by the separation column of the GC enters a metal transfer column through a transfer unit. Two paths are extended from the metal transfer column through a proportional flow divider valve and the two paths extend into the positive-mode reaction region and the negative-mode reaction region through a sidewall of the IMS, respectively. Amounts of the sample in the two paths are adjusted by the proportional flow divider valve such that the sample is supplied to the positive-mode reaction region and the negative-mode reaction region in certain proportion of flow rates. As a result, the proportion of flow rates is adjustable. The metal transfer column exposed between the GC and the IMS may be armored by a heating transfer pipe, so that the metal transfer column between the GC and the IMS is controlled to be maintained at a certain temperature, thereby preventing the sample split-flowing from the GC from condensing in the metal transfer column. Such a structural design achieves an object that the sample bypasses the ionization region. In addition, in the ionization region, molecules in air are ionized by the ionization source and finally form mixed positive and negative reactive ions by a series of electron transfers. In order that the mixed positive and negative reactive ions are separated from each other and respectively enter a positive-mode drift tube and a negative-mode drift tube, two positive and negative horn shaped electrodes may be additionally disposed on both sides of the ionization region, respectively. The reactive ions enter the positive-mode reaction region and the negative-mode reaction region, respectively, under the action of both the horn shaped electrodes and drift carrier gas coming upstream, and are mixed with components of the sample flowing out of the GC in the positive-mode reaction region and the negative-mode reaction region. Sample molecules have different electroaffinities. Therefore, sample molecules having stronger electro negativity are combined with the positive reactive ions to be positively charged in the negative-mode reaction region and are stored in a positive-ion storage region. By opening an ion gate, the positive ions are released into a negative-mode drift region and thus are separated. Likewise, sample molecules having stronger electropositivity are combined with negative reactive ions to be negatively charged in the positive-mode reaction region and are stored in a negative-ion storage region. By opening another ion gate, the negative ions are released into a positive-mode drift region and thus are separated. Drift time information of the ions to be detected is acquired by measuring current signals outputted from Faraday plates at both ends of the IMS and generated by the ions reaching the Faraday plates. Such a structural design not only achieves an object that the sample bypasses the ionization region, but also overcomes the problem of ion destruction due to neutralization reaction among positive and negative ions.

In the embodiment of the present invention, by combining the GC and the dual-mode IMS, on one hand, the GC-IMS system can simultaneously discriminate positive and negative ions so that the system can simultaneously response to all of macromolecules having positive electroaffinity and negative electroaffinity, thereby improving selectivity of the system. On the other hand, a sample to be detected is caused to avoid the ionization region. Even if a conventional radioactive ionization source is adopted, generation of sample molecular ion fragments can be avoided while abundant reactive ions are generated. As a result, the interference signal is reduced and the identifying capability is effectively improved. In addition, a design of distribution by the proportional flow divider valve is adopted at the interface between the GC and the IMS. In this way, the sample is distributed to the positive-mode reaction region and the negative-mode reaction region according to needs. Therefore, not only the positive and negative reactive ions are prevented from being destroyed, but the problem that complicated ions are generated and unidentifiable ion spectrum is formed by interaction between the positive and negative ions is also solved. As a result, both detection sensitivity and resolution of the GC-IMS system are improved. Therefore, the application field of the GC-IMS system can be extended to the range of organic macromolecule samples which are difficult to be detected.

What is claimed is:

1. A GC-IMS system, comprising:
a gas chromatograph,
an IMS comprising: an ionization region for ionizing a gas to generate ions, and a reaction region which is adjacent to and different from the ionization region, is disposed downstream of the ionization region in an ion drift direction, and is configured for combining the ions with a sample,
a sample transfer device which connects the gas chromatograph to the reaction region and is configured to transfer the sample from the gas chromatograph to the reaction region directly by bypassing the ionization region, and
a sweeping gas inlet which is formed in the IMS and is configured to flow a sweeping gas with no sample through the ionization region into the reaction region of the IMS, wherein the ions generated in the ionization region are moved to the reaction region under a sweeping action of the sweeping gas.

2. The GC-IMS system of claim 1, wherein:
the IMS further comprises: an electrode disposed substantially between the ionization region and the reaction region and configured to generate an electric field for moving positive ions or negative ions of the ions generated in the ionization region into the reaction region.

3. The GC-IMS system of claim 1, wherein:
the IMS comprises a dual-mode IMS comprising two reaction regions adjacent to the ionization region, and
the IMS further comprises: two electrodes respectively disposed substantially between the ionization region and one of the two reaction regions and between the ionization region and the other of the two reaction regions, and configured to generate electric fields for respectively moving positive ions and negative ions of the ions generated in the ionization region into the two reaction regions.

4. The GC-IMS system of claim 2, wherein:
the electrode has a horn shape.

5. The GC-IMS system of claim 3, wherein:
the electrode has a horn shape.

6. The GC-IMS system of claim 3, wherein:
the sample transfer device further comprises:
a conduit for transferring the sample; and
a flow divider valve disposed on the conduit and configured to adjust amounts of the sample to be respectively transferred to the two reaction regions.

7. The GC-IMS system of claim 1, wherein:
the gas comprises a carrier gas.

8. The GC-IMS system of claim 7, wherein:
the carrier gas comprises air or nitrogen gas.

9. An IMS, comprising:
an ionization region for ionizing a gas to generate ions,
a reaction region which is adjacent to and different from the ionization region, is disposed downstream of the ionization region in an ion drift direction, and is configured for combining the ions with a sample,
a sample transfer device configured to transfer the sample to the reaction region directly by bypassing the ionization region, and
a sweeping gas inlet configured to flow a sweeping gas with no sample through the ionization region into the reaction region, wherein the ions generated in the ionization region are moved to the reaction region under a sweeping action of the sweeping gas.

10. The IMS of claim 9, further comprising:
an electrode disposed substantially between the ionization region and the reaction region and configured to generate an electric field for moving positive ions or negative ions of the ions generated in the ionization region into the reaction region.

11. The IMS of claim 9, further comprising:
a dual-mode IMS comprising two reaction regions adjacent to the ionization region, and
two electrodes respectively disposed substantially between the ionization region and one of the two reaction regions and between the ionization region and the other of the two reaction regions and configured to generate electric fields for respectively moving positive ions and negative ions of the ions generated in the ionization region into the two reaction regions.

12. The IMS of claim 10, wherein:
the electrode has a horn shaped shape.

13. The IMS of claim 11, wherein:
the electrode has a horn shaped shape.

14. The IMS of claim 9, wherein:
the gas comprises a carrier gas.

15. The GC-IMS system of claim 1, wherein:
the IMS further comprises an ionization source that is a radioactive source.

16. The IMS of claim 9, further comprising:
an ionization source that is a radioactive source.

* * * * *